United States Patent
Teller et al.

(10) Patent No.: US 9,585,458 B2
(45) Date of Patent: Mar. 7, 2017

(54) LIP BALM WITH SPHERICAL SURFACE AND METHOD FOR PRODUCING

(71) Applicant: EOS PRODUCTS, LLC, New York, NY (US)

(72) Inventors: Jonathan Teller, New York, NY (US); Craig Dubitsky, Montclair, NJ (US); Coral Garvey, Brooklyn, NY (US); Dennis Payongayong, Brooklyn, NY (US)

(73) Assignee: EOS PRODUCTS, LLC, New York, NY (US)

( * ) Notice: Subject to any disclaimer, the term of this patent is extended or adjusted under 35 U.S.C. 154(b) by 0 days.

(21) Appl. No.: 15/016,257

(22) Filed: Feb. 4, 2016

(65) Prior Publication Data

US 2016/0262522 A1    Sep. 15, 2016

Related U.S. Application Data

(63) Continuation of application No. 13/941,204, filed on Jul. 12, 2013, now abandoned, which is a
(Continued)

(51) Int. Cl.
*A45D 40/20* (2006.01)
*A45D 40/00* (2006.01)
(Continued)

(52) U.S. Cl.
CPC ......... *A45D 40/0068* (2013.01); *A45D 40/00* (2013.01); *A45D 40/12* (2013.01);
(Continued)

(58) Field of Classification Search
CPC . A45D 2040/0012; A45D 40/12; A49D 40/16
(Continued)

(56) References Cited

U.S. PATENT DOCUMENTS

| 75,524 A | 2/1868 | Chase |
|---|---|---|
| 1,852,455 A | 4/1932 | Friedman |

(Continued)

FOREIGN PATENT DOCUMENTS

| EM | 000031679-0001 | 11/2007 |
|---|---|---|
| EP | 0 433 150 | 6/1991 |

(Continued)

OTHER PUBLICATIONS

U.S. Appl. No. 29/411,931, filed Jan. 2012, Teller.
(Continued)

*Primary Examiner* — Jennifer C Chiang
(74) *Attorney, Agent, or Firm* — Martin & Ferraro, LLP

(57) ABSTRACT

A lip balm applicator product comprises upper and lower portions that are connectable together to define the applicator product being of a substantially spherical shape. A support platform is located in the lower portion and accommodates a quantity of lip balm having an arcuate surface. A lip balm comprises a composition of waxes and oils in solid form and formed to have an arcuate surface. The composition is formed to have the arcuate surface using a hot pour process. A method of manufacturing a lip balm comprises providing a receptacle having a concave arcuate surface. A lip balm material in a heated, liquefied phase is poured into the receptacle. Once poured, the heated, liquefied phase is allowed to solidify such that a surface of the solidified lip balm material has an arcuate configuration that corresponds to the concave arcuate surface of the receptacle.

44 Claims, 4 Drawing Sheets

Related U.S. Application Data continuation of application No. 13/891,268, filed on May 10, 2013, now abandoned, which is a continuation of application No. 12/632,114, filed on Dec. 7, 2009, now Pat. No. 8,444,337.

(51) Int. Cl.

| | | |
|---|---|---|
| *A45D 40/16* | (2006.01) | |
| *A61K 8/31* | (2006.01) | |
| *A61K 8/92* | (2006.01) | |
| *A61Q 19/00* | (2006.01) | |
| *A45D 40/26* | (2006.01) | |
| *B29C 39/02* | (2006.01) | |
| *B65B 5/10* | (2006.01) | |
| *A45D 40/12* | (2006.01) | |
| *A61K 8/97* | (2006.01) | |

(52) U.S. Cl.
CPC .......... *A45D 40/16* (2013.01); *A45D 40/26* (2013.01); *A61K 8/31* (2013.01); *A61K 8/922* (2013.01); *A61K 8/925* (2013.01); *A61K 8/927* (2013.01); *A61K 8/97* (2013.01); *A61Q 19/001* (2013.01); *B29C 39/026* (2013.01); *B65B 5/103* (2013.01); *A45D 2040/0012* (2013.01); *A61K 2800/87* (2013.01)

(58) Field of Classification Search
USPC .............................. 401/49, 88, 98
See application file for complete search history.

(56) References Cited

U.S. PATENT DOCUMENTS

| | | |
|---|---|---|
| D112,545 S | 12/1938 | Younghusband |
| 2,171,112 A | 8/1939 | Hoffman |
| 2,201,467 A | 5/1940 | Bloom |
| D129,291 S | 9/1941 | Petzold |
| D130,030 S | 10/1941 | Meyer |
| 2,314,338 A | 3/1943 | Graves et al. |
| 2,568,688 A | 9/1951 | Sidney |
| 2,745,642 A | 5/1956 | Herman |
| D180,109 S | 4/1957 | Slater |
| 2,859,085 A | 11/1958 | Morrison |
| 2,998,896 A | 9/1961 | Miller |
| 3,085,709 A | 4/1963 | Klein |
| 3,292,840 A | 12/1966 | Schmidt |
| 3,494,515 A | 2/1970 | Fattori |
| D219,496 S | 12/1970 | Lebedeff |
| 3,741,379 A | 6/1973 | Kappler et al. |
| D230,954 S | 3/1974 | Gregorietti |
| 3,843,120 A | 10/1974 | Ricci |
| D240,711 S | 7/1976 | Angleman et al. |
| D243,585 S | 3/1977 | Angleman et al. |
| 4,044,889 A | 8/1977 | Orentreich et al. |
| 4,124,135 A | 11/1978 | Weder et al. |
| D253,394 S | 11/1979 | Berghahn et al. |
| D255,653 S | 7/1980 | Lipsz |
| D255,990 S | 7/1980 | Lucas |
| D256,095 S | 7/1980 | Sandonato |
| 4,235,557 A | 11/1980 | Hayes |
| D258,199 S | 2/1981 | Torongo, Jr. |
| D261,105 S | 10/1981 | Schwartz |
| 4,342,522 A | 8/1982 | Mackles |
| D266,146 S | 9/1982 | Morris |
| 4,369,158 A * | 1/1983 | Woodruff ............... A45D 40/04 264/268 |
| D272,723 S | 2/1984 | Baker |
| D273,766 S | 5/1984 | Lampe |
| D280,289 S | 8/1985 | Aldrich, III et al. |
| D286,616 S | 11/1986 | Becker |
| 4,728,210 A | 3/1988 | Barish et al. |
| 4,765,501 A | 8/1988 | Kao |
| 4,781,483 A | 11/1988 | Lorscheidt |
| D302,384 S | 7/1989 | Holewinski |
| D317,118 S | 5/1991 | Crawford |
| 5,025,817 A | 6/1991 | Wen |
| 5,044,496 A | 9/1991 | Tanaka et al. |
| 5,061,102 A | 10/1991 | Rennie |
| D321,319 S | 11/1991 | Giuseppe |
| 5,092,700 A | 3/1992 | Susini et al. |
| 5,137,185 A | 8/1992 | Mitchell |
| 5,167,462 A | 12/1992 | Lucas |
| D333,780 S | 3/1993 | Jones et al. |
| D333,784 S | 3/1993 | Goodman |
| D339,986 S | 10/1993 | Garouste et al. |
| D343,699 S | 1/1994 | Yang |
| 5,287,979 A | 2/1994 | Bourgeois |
| D346,112 S | 4/1994 | Alcindor |
| D354,441 S | 1/1995 | Fontanella |
| D357,584 S | 4/1995 | Swingier |
| D368,220 S | 3/1996 | Bicknell et al. |
| 5,496,122 A | 3/1996 | Fattori |
| D368,427 S | 4/1996 | Bicknell et al. |
| 5,503,825 A | 4/1996 | Lane |
| 5,542,557 A | 8/1996 | Koyama et al. |
| D377,757 S | 2/1997 | Bertolini |
| D387,662 S | 12/1997 | Bright |
| D389,409 S | 1/1998 | Tucker |
| 5,733,617 A | 3/1998 | Baduel |
| D393,421 S | 4/1998 | Kovens |
| 5,738,123 A | 4/1998 | Szekely |
| 5,743,404 A | 4/1998 | Melashenko et al. |
| 5,792,496 A | 8/1998 | Fekete |
| D398,533 S | 9/1998 | Kotyuk, Jr. et al. |
| 5,799,667 A * | 9/1998 | Szekely ............... A45D 40/16 132/200 |
| 5,808,215 A | 9/1998 | Kralik et al. |
| 5,813,784 A | 9/1998 | Durliat |
| D406,764 S | 3/1999 | Bright et al. |
| 5,884,637 A | 3/1999 | Joulia |
| D408,738 S | 4/1999 | Wu |
| 5,897,263 A | 4/1999 | Fattori |
| 5,925,391 A | 7/1999 | Whetstone, Jr. |
| 5,988,424 A | 11/1999 | Kovens |
| 6,010,264 A | 1/2000 | Scuderi et al. |
| 6,029,842 A | 2/2000 | Sheffler et al. |
| D422,904 S | 4/2000 | Lepsius et al. |
| 6,050,438 A | 4/2000 | Kovens et al. |
| 6,099,872 A | 8/2000 | Whetstone, Jr. |
| 6,193,427 B1 * | 2/2001 | Benguigui ............. A45D 40/16 206/823 |
| D443,726 S | 6/2001 | Faillant-Oumas |
| 6,283,658 B1 | 9/2001 | Estevez et al. |
| 6,391,972 B1 | 5/2002 | Hatakeyama |
| D458,835 S | 6/2002 | Oelli-Venneri |
| D459,216 S | 6/2002 | Heijdenrijk |
| D465,733 S | 11/2002 | Hill |
| D466,252 S | 11/2002 | Yu |
| 6,568,156 B2 | 5/2003 | Silvers et al. |
| D476,111 S | 6/2003 | Karafotas |
| D476,884 S | 7/2003 | Miranda |
| 6,626,313 B2 | 9/2003 | Herbstreit et al. |
| D480,633 S | 10/2003 | Miranda |
| D484,646 S | 12/2003 | Ditrichstein |
| 6,688,795 B1 | 2/2004 | Jacob |
| D489,148 S | 4/2004 | Sheng |
| 6,773,187 B2 | 8/2004 | Gueret |
| D504,979 S | 5/2005 | Lai |
| D507,177 S | 7/2005 | Weissman |
| 7,021,849 B2 | 4/2006 | Ramet |
| D534,076 S | 12/2006 | Green et al. |
| D554,529 S | 11/2007 | Green et al. |
| D561,608 S | 2/2008 | Hogben |
| D562,699 S | 2/2008 | Green et al. |
| D564,900 S | 3/2008 | Green et al. |
| D573,026 S | 7/2008 | Tsai |
| D577,583 S | 9/2008 | Porter et al. |
| D577,584 S | 9/2008 | Porter et al. |
| D578,393 S | 10/2008 | Canamasas Puigbo |
| D592,064 S | 5/2009 | Kilany |
| D592,512 S | 5/2009 | Dubitsky et al. |
| D598,608 S | 8/2009 | Baumer |

(56) References Cited

U.S. PATENT DOCUMENTS

| | | | |
|---|---|---|---|
| D602,663 S | 10/2009 | Pennington | |
| 7,631,781 B2 | 12/2009 | Chen | |
| D608,650 S | 1/2010 | Eisen | |
| D609,103 S | 2/2010 | Marold et al. | |
| D609,107 S | 2/2010 | Dubitsky et al. | |
| D610,458 S | 2/2010 | Martin | |
| D612,245 S | 3/2010 | Canamasas Puigbo | |
| D613,616 S | 4/2010 | Renz et al. | |
| 7,695,727 B2 * | 4/2010 | Magee | A61K 8/0229 424/401 |
| 7,699,062 B2 | 4/2010 | Sasaki | |
| D615,818 S | 5/2010 | Jansen | |
| D618,397 S | 6/2010 | Dubitsky et al. | |
| D618,398 S | 6/2010 | Dubitsky et al. | |
| D625,469 S | 10/2010 | Dubitsky | |
| D631,204 S | 1/2011 | Dubitsky et al. | |
| 7,878,793 B2 | 2/2011 | Quillin et al. | |
| D644,939 S | 9/2011 | Teller | |
| 8,444,337 B2 | 5/2013 | Teller | |
| 8,651,308 B1 | 2/2014 | Sung | |
| 8,747,002 B2 | 6/2014 | Izkovitz | |
| D710,544 S | 8/2014 | Shen | |
| 8,888,391 B2 | 11/2014 | Teller et al. | |
| 9,232,844 B2 | 1/2016 | Thompson | |
| D748,976 S | 2/2016 | Mitchell | |
| 2002/0003983 A1 | 1/2002 | Gueret | |
| 2002/0008105 A1 | 1/2002 | Herbstreit et al. | |
| 2003/0077102 A1 | 4/2003 | Bourjal | |
| 2003/0161851 A1 | 8/2003 | Breha, III et al. | |
| 2003/0201201 A1 | 10/2003 | Cheng | |
| 2004/0005186 A1 | 1/2004 | Ueda et al. | |
| 2006/0076033 A1 | 4/2006 | Bouix | |
| 2006/0201838 A1 | 9/2006 | Sasaki | |
| 2006/0254945 A1 | 11/2006 | Green et al. | |
| 2007/0017915 A1 | 1/2007 | Weder et al. | |
| 2007/0108092 A1 | 5/2007 | Minuto et al. | |
| 2007/0280773 A1 | 12/2007 | Warren | |
| 2008/0019758 A1 | 1/2008 | Mallardi | |
| 2008/0110854 A1 | 5/2008 | Kelly | |
| 2008/0131187 A1 | 6/2008 | Breidenbach et al. | |
| 2008/0213028 A1 | 9/2008 | Hosokawa et al. | |
| 2009/0022541 A1 | 1/2009 | De LaForcade | |
| 2009/0028625 A1 | 1/2009 | Bonneyrat | |
| 2011/0024316 A1 | 2/2011 | Ginsburg | |
| 2011/0135377 A1 | 6/2011 | Teller | |
| 2011/0253731 A1 | 10/2011 | Smith | |
| 2013/0302080 A1 | 11/2013 | Teller et al. | |
| 2013/0322950 A1 | 12/2013 | Teller | |
| 2013/0330427 A1 | 12/2013 | Smigel et al. | |
| 2013/0341832 A1 | 12/2013 | Teller et al. | |
| 2013/0341833 A1 | 12/2013 | Teller et al. | |
| 2014/0013712 A1 | 1/2014 | Teller | |
| 2014/0105666 A1 | 4/2014 | Teller | |
| 2015/0037082 A1 | 2/2015 | Pires et al. | |
| 2015/0182004 A1 | 7/2015 | Teller et al. | |

FOREIGN PATENT DOCUMENTS

| | | |
|---|---|---|
| EP | 0 628 393 | 4/1994 |
| ES | 0505578-01 | 11/2007 |
| FR | 2563711 | 5/1984 |
| FR | 0628393 | 4/1994 |
| FR | 2726443 | 3/1995 |
| FR | 2766339 | 7/1997 |
| FR | 2925263 | 12/2007 |
| GB | 2162822 | 5/1985 |
| GB | 2007213 | 5/1990 |
| JP | 1136041 | 3/2002 |
| JP | 455237-001 | 6/2003 |
| JP | 1175238 | 6/2003 |
| JP | 2004106932 | 4/2004 |
| JP | 2001321140 | 11/2004 |
| JP | 2004321410 | 11/2004 |
| JP | 2006-204821 | 9/2006 |
| KR | 20090006972 | 1/2009 |
| WO | WO 2007/007288 | 1/2007 |

OTHER PUBLICATIONS

U.S. Appl. No. 29/411,933, filed Jan. 2012, Teller.
U.S. Appl. No. 13/891,264, filed May 2013, Teller.
U.S. Appl. No. 14/973,717, filed Dec. 2015, Teller.
U.S. Appl. No. 14/988,740, filed Jan. 2016, Teller.
*eos Products LLC* v. *Oralabs, Inc. et al.* Complaint in US District Court for the District of Delaware; Jun. 4, 2015.
eos Products LLC and The Kind Group LLC Complaint against Oralabs, Inc. et al. in US International Trade Commission; Jun. 12, 2015.
Claim Chart for CVS products; Jun. 12, 2015.
Claim Chart for Dollar Tree products; Jun. 12, 2015.
Claim Chart for Five Below products; Jun. 12, 2015.
Claim Chart for Walgreens products; Jun. 12, 2015.
Claim Chart for Domestic Industry products; Jun. 12, 2015.
Third Party Observations in Application No. EP20100836463; Jun. 15, 2015.
Letter from Oralab's Counsel regarding ITC Case; Jul. 20, 2015.
CVS Response to ITC Complaint; Aug. 24, 2015.
Five Below Response to ITC Complaint; Aug. 24, 2015.
Walgreens' Response to ITC Complaint; Aug. 24, 2015.
Respondents' First Set of Interrogatories to Complainants; Aug. 27, 2015.
International Search Report for PCT/US2010/059025 dated Aug. 31, 2011; 2 pages.
Lancome Baume Baiser (date unclear—for purpous of examination—please consider as prior art).
Letter from John L. Welsh enclosing Draft IPR Petition; Jul. 27, 2015.
Office Action dated Mar. 20, 2015, received in related application No. 201080063211 pending in SIPO.
SIPO Office Action issued Jul. 17, 2014 in connection with CN Appl. No. 201080063211.X JP 2004-321410A and JP 1136041S (listed separately).
Webpage from www.amazon.com showing "Lancome Baume Baiser Hydrating Balm Sensual Massage for Lips" product and images (3 pages).
Webpage http://www.musingsofamuse.com/2009/10/beauty-on-a-budget-eos-lip-b- alm-review.html,Oct. 1, 2009.
EP 2509461 Observations by Third Parties; Jan. 16, 2014.
EP 2509461 Office Action; Oct. 10, 2014.
EP 2509461 Office Action; May 26, 2015.
EP 2509461 Observations by Third Parties; Jun. 9, 2015.
Letter from Oralabs' Counsel regarding ITC Case; Sep. 9, 2015.
Office Action in CN201080063211; Oct. 8, 2015.
EP 2509461 Observations by Third Parties; Oct. 28, 2015.
EP 2509461 Observations by Third Parties; Jan. 29, 2016.
EP 2509461 Observations by Third Parties; Mar. 7, 2016.
Office Action in CN201510024881.5; Apr. 5, 2016.
EP 2509461 Observations by Third Parties; Jun. 30, 2016.
Office Action in EP16166294.5-1653; Aug. 11, 2016.
Office Action in CN201510024881.5; Aug. 23, 2016.
Office Action in U.S. Appl. No. 12/632,114; Jul. 2, 2012.
Office Action in U.S. Appl. No. 12/632,114; Nov. 30, 2012.
Notice of Allowance in U.S. Appl. No. 12/632,114; Apr. 18, 2013.
Office Action in U.S. Appl. No. 13/891,268; Apr. 30, 2015.
Office Action in U.S. Appl. No. 13/941,228; Dec. 2, 2013.
Office Action in U.S. Appl. No. 13/941,228; Apr. 21, 2014.
Notice of Allowance in U.S. Appl. No. 13/941,228; Aug. 27, 2014.
Office Action in U.S. Appl. No. 13/941,060; Dec. 2, 2013.
Office Action in U.S. Appl. No. 13/941,060; Jul. 15, 2014.
Office Action in U.S. Appl. No. 13/941,060; Nov. 19, 2014.
Office Action in U.S. Appl. No. 13/941,060; Apr. 17, 2015.
Office Action in U.S. Appl. No. 13/941,204; Mar. 25, 2015.
Notice of Allowance in U.S. Appl. No. 13/941,204; Nov. 5, 2015.
Office Action in U.S. Appl. No. 13/972,893; Nov. 5, 2013.
Office Action in U.S. Appl. No. 13/972,893; Mar. 4, 2014.

(56) References Cited

OTHER PUBLICATIONS

Office Action in U.S. Appl. No. 13/972,893; Jun. 18, 2014.
Office Action in U.S. Appl. No. 13/972,893; Sep. 24, 2014.
Office Action in U.S. Appl. No. 13/972,893; Mar. 31, 2015.
Office Action in U.S. Appl. No. 13/972,893; Jul. 29, 2015.
Office Action in U.S. Appl. No. 13/972,896; Mar. 5, 2014.
Notice of Allowance in U.S. Appl. No. 13/972,896; Aug. 1, 2014.
Notice of Allowance in U.S. Appl. No. 13/972,896; Nov. 6, 2014.
Notice of Allowance in U.S. Appl. No. 13/972,896; Feb. 13, 2015.
Notice of Allowance in U.S. Appl. No. 13/972,896; Sep. 18, 2015.
Office Action in U.S. Appl. No. 13/972,896; May 27, 2015.
Office Action in U.S. Appl. No. 13/972,896; Jul. 16, 2015.
Office Action in U.S. Appl. No. 13/972,898; Mar. 7, 2014.
Office Action in U.S. Appl. No. 13/972,898; Jun. 23, 2015.
Notice of Allowance in U.S. Appl. No. 13/972,898; Aug. 1, 2014.
Notice of Allowance in U.S. Appl. No. 13/972,898; Oct. 17, 2014.
Notice of Allowance in U.S. Appl. No. 13/972,898; Dec. 11, 2014.
Notice of Allowance in U.S. Appl. No. 13/972,898; Feb. 2, 2015.
Notice of Allowance in U.S. Appl. No. 13/972,898; May 14, 2015.
Notice of Allowance in U.S. Appl. No. 13/972,898; Jul. 21, 2015.
Notice of Allowance in U.S. Appl. No. 13/972,898; Jul. 27, 2015.
Notice of Allowance in U.S. Appl. No. 13/972,898; Oct. 6, 2015.
Born Pretty Store, "50Pcs/set Dry Wet Amphibious Sponge Powder Puff Round Rectangle Puff Beauty Makeup Tool", Accessed Nov. 14, 2016. (http://www.bornprettystore.com/50pcsset-amphibious-sponge-powder-puffround-rectangle-puff-beauty-makeup-tool-p-34825.html).
Born Pretty Store, "1Pc Pro Powder Puff Beauty Cute Egg Shape Sponge Make-up Foundation Makeup (Random Color)", Accessed Nov. 14, 2016. (http://www.bornprettystore.com/powder-puff-beauty-cute-shapesponge-make-foundation-makeuprandom-color-p-20027.html).

\* cited by examiner

LIP BALM WITH SPHERICAL SURFACE AND METHOD FOR PRODUCING

The present application is a continuation of U.S. application Ser. No. 13/941,204, filed Jul. 12, 2013; which is a continuation of U.S. application Ser. No. 13/891,268, filed May 10, 2013 (now abandoned); which is a continuation of U.S. application Ser. No. 12/632,114, filed Dec. 7, 2009 (now U.S. Pat. No. 8,444,337); all of which are incorporated by reference herein.

TECHNICAL FIELD

The present invention relates to lip balms and, more particularly, a lip balm having a spherical surface and manufactured using a hot pour process.

BACKGROUND

Skin on and around the lips can often become chapped or otherwise damaged due to overexposure from elements such as sun and/or wind, particularly during athletic activities in which a person's face remains exposed to these elements for extended periods of time. The same skin can also become chapped or damaged while carrying out everyday non-athletic activities. For example, working outside in extreme cold, dry heat, or sun can also cause damage to the skin on the lips. Even working indoors or sleeping in dry conditions can cause the lips to chap, thereby leading to the development of cracks, which are often painful and can become infected.

Lip balms are often applied to prevent chapped lips. When applied prior to exposure to sun, wind, dry heat, or other extreme conditions, the lip balm can provide suitable protection to the skin on and around the lips. Even when applied after the skin on the lips is chapped, the lip balm can prevent any further damage from occurring. In either case, by providing a protective layer of lip balm, the risk of an infection developing in the damaged skin is minimized.

Lip balms are currently sold as emulsions, liquids, gels, or solids. In emulsion or liquid form, the lip balms are generally packed in containers such as jars. Gels (and liquids on occasion) are typically dispensed from squeeze tubes. Solid lip balms are generally packaged in stick form and dispensable from tubes or from lipstick-type applicators.

Solid lip balms are commonly manufactured using either a hot pour process or a bullet process. In the hot pour process, the lip balm ingredients are combined and heated in a liquefied phase. The liquid is then directly poured into the final consumer package, where it is cooled and solidifies. In the bullet process, the lip balm ingredients are also combined and heated in a liquefied phase. However, in the bullet process, the liquefied balm is poured into molds where it is cooled and solidified. The balm may then be cut into the desired shape and inserted into the consumer package.

The choice of the method used for a particular product depends on the design/functionality of the package, the additives in the balm, and the desired characteristics of the lip balm (color, feel, shape, and the like).

SUMMARY

In one aspect, the present invention resides in a lip balm applicator product that is substantially spherical in shape. The applicator product comprises upper and lower portions that are connectable together to define the substantially spherical shape of the applicator product. A support platform is located in the lower portion and accommodates a quantity of lip balm having an arcuate surface that can be exposed upon separation of the upper portion from the lower portion.

In another aspect, the present invention resides in a lip balm product comprising a composition of waxes and oils in solid form and formed to have an arcuate surface. The wax and oil composition can be eroded upon being drawn across a surface such as a user's lips. The composition is formed to have the arcuate surface using a hot pour process.

In another aspect, the present invention resides in a method of manufacturing a lip balm. In such a method, a receptacle having a concave arcuate surface is provided. A lip balm material in a heated, liquefied phase is also provided and poured into the receptacle. Once poured, the heated, liquefied phase is allowed to solidify such that a surface of the solidified lip balm material has an arcuate configuration that corresponds to the concave arcuate surface of the receptacle.

DETAILED DESCRIPTION

Figure 1:
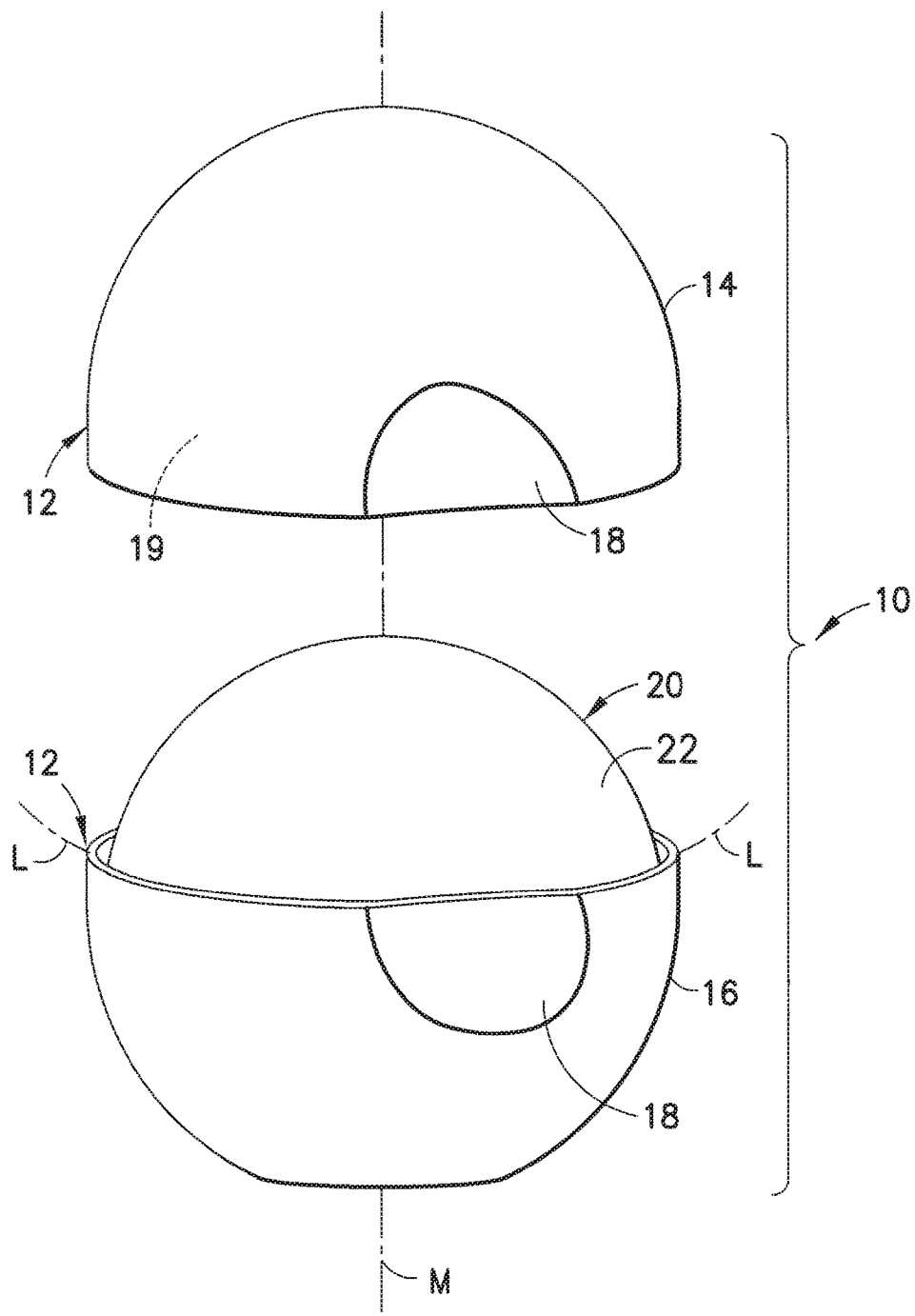
FIG. 1 is a perspective view of a lip balm applicator, of the present invention.

As is shown in FIG. 1, a lip balm applicator product having a lip balm composition is designated generally by the reference number 10 and is hereinafter referred to as "applicator 10." Applicator 10 comprises a receptacle 12 having the lip balm composition located therein. The receptacle 12 is substantially spherical in shape. The present invention is not limited in this regard, as the receptacle 12 may be substantially cylindrical with rounded surfaces, egg-shaped, ovate, or the like. The receptacle 12 comprises an upper portion 14 and a lower portion 16, the portions being separable from each other along a line L that extends substantially circumferentially about the receptacle perpendicular to a major axis M extending longitudinally through the receptacle. An interior surface 19 of the upper portion 14 of the receptacle 12 is defined by a concave surface having a spherical or arcuate topography. Although various surfaces described herein are referred to as being spherical, it should be understood that the term "spherical" includes arcuate surfaces.

The upper portion 14 and the lower portion 16 are connectable together via any suitable means such as the interengagement of threads. The present invention is not limited in this regard, as other mechanisms may be used to connect the upper portion 14 and the lower portion 16 together (e.g., engaging surfaces that fit together frictionally). The lip balm composition is located in the lower portion 16 and is hereinafter referred to as "lip balm 20."

The outer surface of the receptacle 12 includes a depression 18 formed partly on the upper portion 14 and partly on the lower portion 16. The depression 18 is a divot formed in the receptacle 12 that accommodates the thumb of a user to facilitate the opening and closing of the receptacle by alternatingly separating and connecting the upper portion 14 and the lower portion 16.

Upon separation of the upper portion 14 from the lower portion 16, the lip balm 20 is revealed. The lip balm 20 is mounted in the lower portion 16 on a support platform and is defined by a quantity of suitable lip balm material formed or otherwise configured to have a spherical shape that includes a spherical surface 22. The spherical shape and spherical surface 22 allows the lip balm material to extend above the upper edge of the lower portion 16, thereby facilitating the uninhibited application of the lip balm to a user's lips. The present invention is not limited to the lip balm 20 being configured to have a spherical shape and spherical surface 22, however, as other configurations are within the scope of the present invention.

Figure 2:
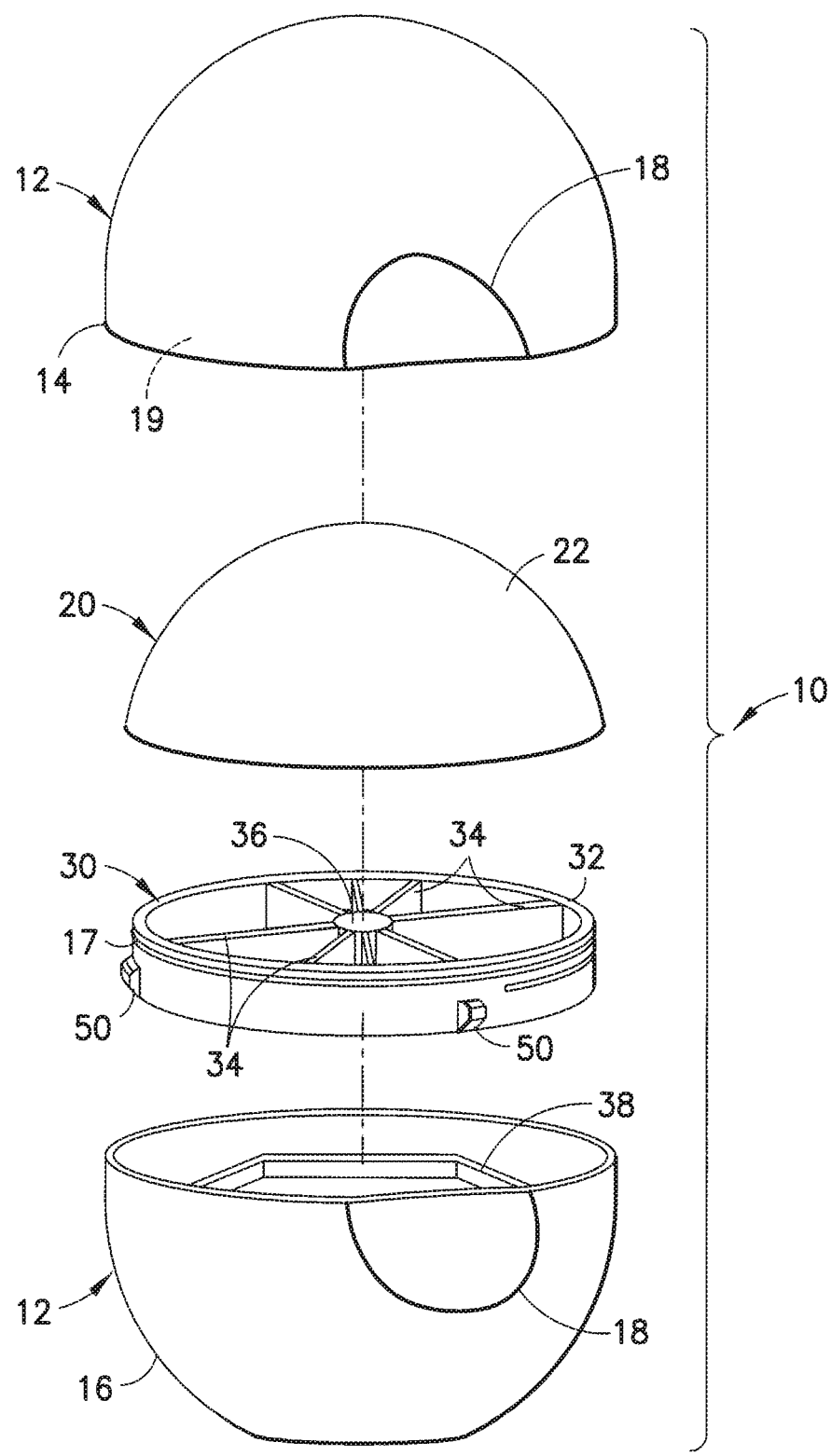
FIG. 2 is a perspective exploded view of the lip balm applicator of FIG. 1.

Referring now to FIG. 2, the support platform on which the lip balm 20 is mounted is designated generally by the reference number 30. The support platform 30 is a wheel having an outer rim 32 and threads 17 located thereon. A plurality of prongs 50 is located along a lower edge of the outer rim 32 (the edge opposite the threads 17) to facilitate the connection of the support platform 30 to connecting structure such as ridges 38 in the lower portion 16. In the assembly of the receptacle 10, the prongs 50 allow the support platform 30 to be snapplingly received on lower portion 16.

The support platform 30 includes a plurality of spokes 34 that extend from the outer rim 32 and that terminate at a hub 36. Both the widths of the spokes 34 and the diameter of the hub 36 are selected to provide a suitable area on which the lip balm 20 can be supported. The spokes 34 extend from the hub 36 at equal angles and connect with an inner surface of the outer rim 32. The present invention is not limited to the use of spokes and hubs, as the area bounded by the outer rim 32 can be solid. Although the outer rim 32 is described as being substantially circular, a portion along the edge of the outer rim is flattened to allow for the accommodation of the depression 18.

Figure 3:
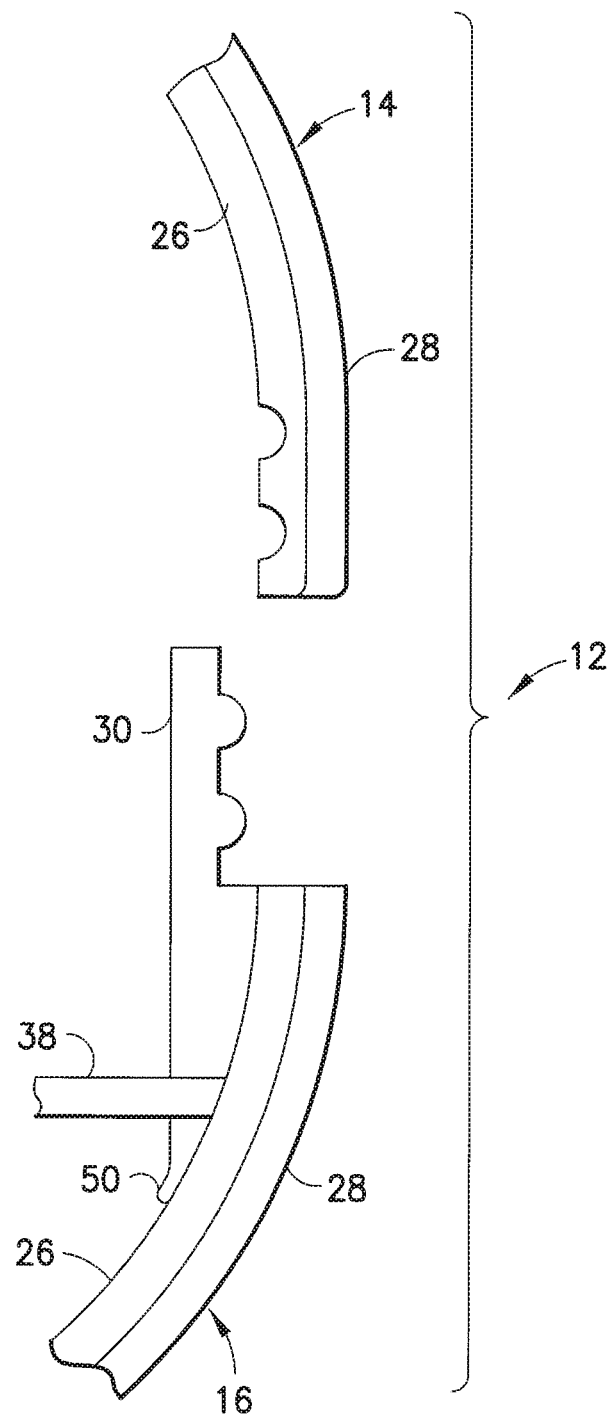
FIG. 3 is a schematic view of a portion of a receptacle of the lip balm applicator of FIG. 1.

Referring now to FIG. 3, both the upper portion 14 and the lower portion 16 of the receptacle 12 comprise a thermoplastic elastomer (TPE) injection molded over a plastic form comprising acrylonitrile-butadiene-styrene (ABS) copolymer. Accordingly, the defining surfaces of both the upper portion 14 and the lower portion 16 comprise a bottom layer 26 of ABS copolymer covered by a top layer 28 of TPE. The present invention is not limited to the bottom layer 26 being ABS copolymer, however, as the bottom layer in one or both of the upper portion 14 and the lower portion 16 can be polyethylene (PE). In such an alternate configuration, the tactile sensation to the user is slightly different upon handling the receptacle 12. In any configuration, the material of the top layer 28 provides a desirable tactile sensation to the user of the applicator 10, namely, by providing a soft surface that can be easily gripped, thereby facilitating the easy opening and closing of the receptacle 12.

The lip balm 20 comprises a quantity of suitable lip balm material. One exemplary lip balm material is a composition that is at least in part a blend of beeswax, coconut oil, olive oil, and jojoba oil that can be eroded when drawn over a surface (e.g., lips). The present invention is not limited to the lip balm material being a blend of such wax and oils, however, as other materials (e.g., petrolatum and petrolatum-based compounds) are within the scope of this disclosure. The blend of beeswax, coconut oil, olive oil, and jojoba oil can also include various ingredients including, but not limited to, emollients, ultraviolet protective agents, moisturizers, vitamins, aloe vera, colorants, fragrances, and the like. Drawing the material over a surface such as the lips causes the material to transfer to the surface as a film.

The spherical outer surface 22 of the lip balm 20 defines a mound-shaped quantity of the lip balm material. The spherical or mound shape provides desirable tactile sensations and use benefits as compared to stick (tubular) forms of the lip balm material. Desirable tactile sensations result from the spherical shape having a larger exposed surface area (as compared to the stick forms of the lip balm material) and the tactile sensation of a curved surface against the lips. Use benefits include the ability to apply the lip balm material to both lips simultaneously.

Figure 4:
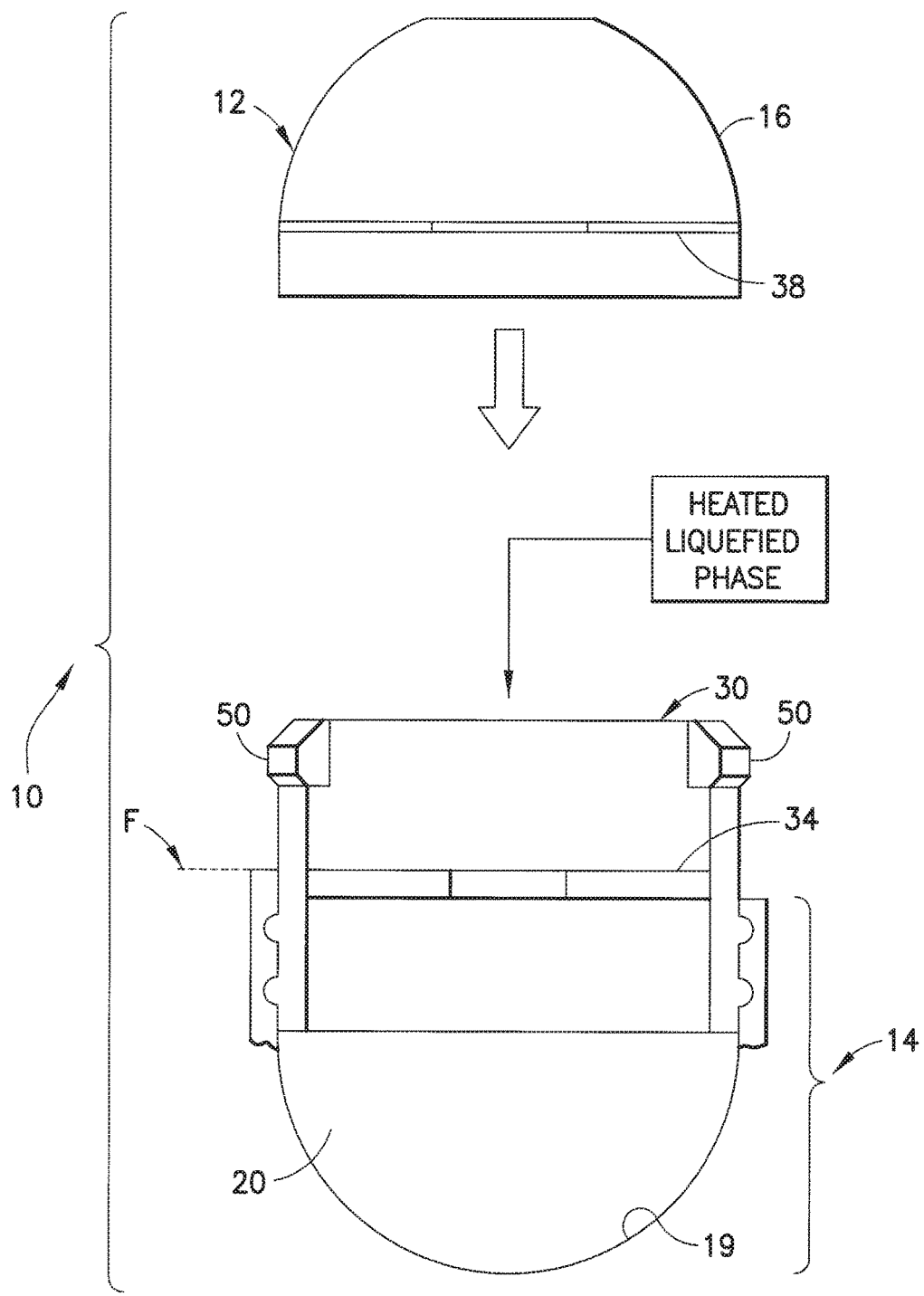
FIG. 4 is a schematic representation of a hot pour process of manufacturing a lip balm having an arcuate surface.

Referring now to FIG. 4, the lip balm 20 is manufactured from the lip balm material using a hot pour process. In using the hot pour process, the lip balm ingredients are combined and heated in a liquefied phase and poured into the final consumer packaging, which in this case is the receptacle 12. In preparation for the hot pour process, the support platform 30 is assembled with the upper portion 14 and inverted such that the support platform is level and vertical with regard to the upper portion. Orienting the assembled upper portion 14 and support platform 30 in this manner allows for the heated and liquefied phase to be poured into the upper portion and retained therein. The interior surface 19 of the upper portion 14 may be coated with a release agent prior to pouring the heated and liquefied phase, which thereby allows for efficient and clean removal of the upper portion by the user when using the finished product.

After the heated and liquefied phase is poured into the upper portion 14 and filled to a level F to cover at least a portion of the spokes 34, the liquefied phase is cooled or allowed to cool. The spokes 34 provide surfaces onto which the solidified lip balm material can adhere. The present invention is not limited to the solidification of the lip balm material around spokes, however, as the support platform can include any suitable configuration of surfaces around which the lip balm material can solidify. Upon sufficient solidification of the lip balm material, the lower portion 16 is inserted onto the assembled and filled upper portion 14 and support platform 30.

The use of the hot pour method in manufacturing the lip balm 20 defined by the spherical surface 22 provides cost benefits over similar methods that use the bullet method. In particular, using the hot pour method obviates the need for an intermediate step in which hot liquid is poured into separate molds, thereby also eliminating the need for additional equipment (molds). Furthermore, the additional steps of removing solidified product from molds and processing and handling the solidified product are avoided.

Although this invention has been shown and described with respect to the detailed embodiments thereof, it will be understood by those of skill in the art that various changes may be made and equivalents may be substituted for elements thereof without departing from the scope of the invention. In addition, modifications may be made to adapt a particular situation or material to the teachings of the invention without departing from the essential scope thereof. Therefore, it is intended that the invention not be limited to the particular embodiments disclosed in the above detailed description, but that the invention will include all embodiments falling within the scope of this disclosure.

We claim:

1. A method of manufacturing a lip balm applicator comprising:

pouring liquefied phase lip balm into an upper portion of a lip balm enclosure, the lip balm enclosure comprising:

the upper portion releasably attachable to a sub-assembly, the sub-assembly comprising:

a lower portion having an interior surface and an exterior surface, and a support structure connected to the interior surface of the lower portion, the support structure comprising a plurality of surfaces extending radially inward from the interior surface of the lower portion; and solidifying the lip balm such that the lip balm is attached to and mounted on the support structure, the lip balm extending into the upper portion when the upper portion is attached to the sub-assembly;

wherein the upper portion is releasably attached to the sub-assembly with interlocking threads.

2. The method of claim 1, wherein an exterior shape of the solidified lip balm substantially matches a shape of an interior surface of the upper portion.

3. The method of claim 1, wherein the upper portion comprises an inner layer and an outer layer.

4. The method of claim 3, wherein at least one of the inner layer or the outer layer comprises a thermoplastic elastomer.

5. The method of claim 3, wherein the outer layer is softer than the inner layer.

6. The method of claim 3, wherein the inner layer comprises a releasing agent.

7. The method of claim 1, wherein the support structure is substantially circular.

8. The method of claim 1, wherein the lip balm applicator is symmetrical about a major axis of the lip balm enclosure.

9. The method of claim 1, wherein the solidified lip balm comprises an arcuate surface.

10. The method of claim 1, wherein the solidified lip balm comprises a spherical surface.

11. The method of claim 1, wherein the solidified lip balm has an exterior shape that complements the upper portion of the lip balm enclosure.

12. The method of claim 1, wherein the lip balm comprises petrolatum.

13. The method of claim 1, wherein the lip balm comprises at least one moisturizer.

14. The method of claim 1, wherein the lip balm comprises at least one ultraviolet protective agent.

15. A method of manufacturing a lip balm applicator comprising:

pouring liquefied phase lip balm into an upper portion of a lip balm enclosure, the lip balm enclosure comprising:

the upper portion releasably attachable to a sub-assembly, the sub-assembly comprising:

a lower portion having an interior surface and an exterior surface, and a support structure connected to the interior surface of the lower portion, the support structure comprising at least one surface extending inward from the interior surface of the lower portion; and solidifying the lip balm such that the lip balm is attached to and mounted on the support structure, the lip balm extending into the upper portion when the upper portion is attached to the sub-assembly;

wherein the upper portion is releasably attached to the sub-assembly with interlocking threads.

16. The method of claim 15, wherein an exterior shape of the solidified lip balm substantially matches a shape of an interior surface of the upper portion.

17. The method of claim 15, wherein the upper portion comprises an inner layer and an outer layer.

18. The method of claim 17, wherein at least one of the inner layer or the outer layer comprises a thermoplastic elastomer.

19. The method of claim 17, wherein the outer layer is softer than the inner layer.

20. The method of claim 17, wherein the inner layer comprises a releasing agent.

21. The method of claim 15, wherein the support structure is substantially circular.

22. The method of claim 15, wherein the lip balm applicator is symmetrical about a major axis of the lip balm enclosure.

23. The method of claim 15, wherein the solidified lip balm comprises an arcuate surface.

24. The method of claim 15, wherein the solidified lip balm comprises a spherical surface.

25. The method of claim 15, wherein the solidified lip balm has an exterior shape that complements the upper portion of the lip balm enclosure.

26. The method of claim of claim 15, wherein the lip balm comprises petrolatum.

27. The method of claim of claim 15, wherein the lip balm comprises at least one moisturizer.

28. The method of claim of claim 15, wherein the lip balm comprises at least one ultraviolet protective agent.

29. A method of making a lip balm applicator comprising:

selecting packaging for the lip balm applicator, wherein the packaging comprises a mold portion having threads on an interior surface, and a lower portion having threads on an exterior surface and a lip balm support structure connected to an interior surface of the lower portion;

orienting at least the mold portion of the packaging to receive and retain a heated liquefied phase lip balm;

pouring the heated liquefied phase lip balm through the lip balm support structure into the mold portion; and solidifying the lip balm such that the lip balm is attached to and mounted on the support structure, the lip balm extending into the mold portion when the mold portion is attached to the lower portion;

wherein when the packaging is assembled, the lip balm is revealed by disengaging the threads located on the interior surface of the mold portion from the threads located on the exterior surface of the lower portion.

30. The method of claim 29, wherein an exterior shape of the solidified lip balm substantially matches a shape of the interior surface of the mold portion.

31. The method of claim 29, wherein the mold portion comprises an inner layer and an outer layer.

32. The method of claim 31, wherein at least one of the inner layer or the outer layer comprises a thermoplastic elastomer.

33. The method of claim 31, wherein the outer layer is softer than the inner layer.

34. The method of claim 31, wherein the inner layer comprises a releasing agent.

35. The method of claim 29, wherein the support structure is substantially circular.

36. The method of claim 29, wherein the lip balm applicator is symmetrical about a major axis of the lip balm applicator.

37. The method of claim 29, wherein the solidified lip balm comprises an arcuate surface.

38. The method of claim 29, wherein the solidified lip balm comprises a spherical surface.

39. The method of claim 29, wherein the solidified lip balm has an exterior shape that complements the mold portion of the packaging.

40. The method of claim 29, wherein the lip balm comprises petrolatum.

41. The method of claim 29, wherein the lip balm comprises at least one moisturizer.

42. The method of claim 29, wherein the lip balm comprises at least one ultraviolet protective agent.

43. The method of claim 29, wherein the support structure comprises at least one surface extending inward relative to an interior surface of the lower portion.

44. The method of claim 29, wherein the support structure comprises a plurality of surfaces extending radially inward relative to the interior surface of the lower portion.

* * * * *

UNITED STATES PATENT AND TRADEMARK OFFICE
CERTIFICATE OF CORRECTION

PATENT NO. : 9,585,458 B2  
APPLICATION NO. : 15/016257  
DATED : March 7, 2017  
INVENTOR(S) : Jonathan Teller et al.

Page 1 of 1

It is certified that error appears in the above-identified patent and that said Letters Patent is hereby corrected as shown below:

On the Title Page

Page 3, Item (56) References Cited, Other Publications:
Column 2, Line 29: change "purpous" to -- purpose --; and
Column 2, Line 42: change "budget-eos-lip-b- alm-review.html,Oct. 1, 2009." to
-- budget-eos-lip-balm-review.html, Oct. 1, 2009. --.

Page 4, Item (56) References Cited, Other Publications:
Line 27: change "sponge-power-puffround-rectangle-puff-beauty-makeup-tool-p-" to
-- sponge-power-puff-round-rectangle-puff-beauty-makeup-tool-p- --; and
Line 32: change "beauty-cute-shapesponge-make-foundation-makeuprandom-color-" to
-- beauty-cute-shape-sponge-make-foundation-makeuprandom-color- --.

In the Claims

Column 6, Claims 26, 27, and 28:
Lines 20, 22, and 24: delete "of claim" (first occurrence).

Signed and Sealed this  
Twelfth Day of February, 2019

Andrei Iancu  
*Director of the United States Patent and Trademark Office*